(12) United States Patent
Cummins et al.

(10) Patent No.: US 6,462,213 B1
(45) Date of Patent: Oct. 8, 2002

(54) METAL NITRIDO COMPLEXES

(75) Inventors: Christopher C. Cummins, Cambridge, MA (US); Catalina E. Laplaza, Somerville, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 09/484,952

(22) Filed: Jan. 18, 2000

Related U.S. Application Data

(62) Division of application No. 08/841,283, filed on Apr. 29, 1997, now Pat. No. 6,037,459.
(60) Provisional application No. 60/016,553, filed on Apr. 30, 1996.

(51) Int. Cl.[7] .............................. C07F 11/00; B01J 31/00
(52) U.S. Cl. .............................. 556/57; 556/1; 556/42; 556/51; 534/11
(58) Field of Search .............................. 556/42, 51, 57, 556/1; 534/11

(56) References Cited

PUBLICATIONS

Laplaza et al., Journal of American Chemical Society, vol. 118, No. 36, pp. 8623–8638 (Sep. 11, 1996).*

Zewdu et al., Chemical Anstracts, vol. 115, No. 16, p. 991, abstract No. 173314b, Oct. 1991.*

* cited by examiner

Primary Examiner—Porfirio Nazario-Gonzalez
(74) Attorney, Agent, or Firm—Choate, Hall & Stewart, LLP

(57) ABSTRACT

A method for the generation of ammonia from dinitrogen is provided including reacting a three coordinate, low oxidation state transition metal complex with dinitrogen under substantially atmospheric pressures to obtain a metal-nitrido complex, whereby the oxidation state of the metal complex increases, and reducing the metal of the metal nitrido complex in the presence of a hydrogen source, so as to obtain $NH_3$. A novel metal complex is provided which is capable of cleaving small molecules which includes a metal selected from the group consisting of molybdenum, titanium, vanadium, niobium, tungsten, uranium and chromium. The compound may have the formula $M(NR_1R_2)_3$ where M is a transition metal; $R_1$ and $R_2$ are independently selected from the group consisting of tertiary alkyls, phenyls and substituted phenyls. The compound permits cleavage of nitrogen-nitrogen triple bonds.

10 Claims, 4 Drawing Sheets

(1)

METAL NITRIDO COMPLEXES

This application is a divisional application of patent application Ser. No. 08/841,283 entitled "dinitrogen cleavage" filed on Apr. 29, 1997, now U.S. Pat. No. 6,037,459 which claims priority to provisional application No. 60/016,553 filed on Apr. 30, 1996, entitled "Bond Activation By Three-Coordinate Metal Complexes", both of which are incorporated in their entirety by reference.

BACKGROUND OF THE INVENTION

Cleavage of the relatively inert dinitrogen ($N_2$) molecule, with its extremely strong N≡N triple bond, has represented a major challenge to the development of $N_2$ chemistry. The relatively inert dinitrogen molecule ($N_2$) composes 78% of the Earth's atmosphere; the development of this molecule's chemistry is clearly desirable if this immense natural resource is to be utilized optimally. In this regard, the discovery of mild methods for scission of the N≡N triple bond represents a major challenge.

The Haber-Bosch ammonia synthesis is the premier example of industrial nitrogen fixation. This process reacts hydrogen and nitrogen at high temperatures and pressures, in the presence of an iron catalyst to produce ammonia, according to eq. (1),

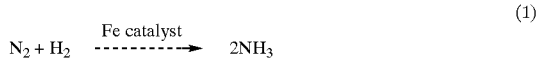
(1)

Based on recent ultraviolet photoelectron spectroscopy and x-ray photoelectron spectroscopy studies, the following mechanism has been proposed for the formation of ammonia, whereby the nitrogen can be adsorbed on an iron surface in both the atomic and molecular states.

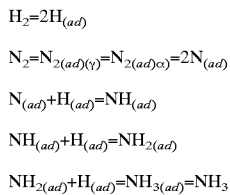

Unfortunately, typical operating temperatures and pressures are in the range of 400–550° C. and 100–1000 atm, respectively, thus rendering this process extremely dangerous. Additionally, the necessary equipment for this process is very large and expensive. Naturally, the development of processes at lower temperatures and pressures, preferably standard pressure and temperature, would be economically very attractive, and would reduce the danger involved.

Several modifications of the Haber-Bosch process, such as the Kellogg Ammonia Process, the Topsoe Ammonia Process, the ICI AMV Ammonia Process, and the Braun Purifier Process, have attempted to address these concerns, and have succeeded in increasing efficiency while modestly lowering the temperatures and pressures required (350–470° C., 70–105 bar). (C. Hooper, in *Catalytic Ammonia Synthesis*, J. R. Jennings, Ed. Plenum, New York, 1991). However, these processes still operate at very high temperatures and pressures and the equipment involved is still very specialized, large, and expensive. Thus, there is a continuing interest in developing a catalyst system that would operate at standard temperature and pressure.

The metalloenzyme nitrogenase constitutes a unique biological nitrogen-fixing system capable of nitrogen triple bond cleavage at ambient temperatures and pressures. Nitrogenase catalyzes the reduction of molecular nitrogen to ammonia together with the production of dihydrogen under mild conditions, according to eq. (2), $$N_2 + 8H^+ + 8e^- \longrightarrow 2NH_3 + H_2 \qquad (2)$$

For many years effort has been expounded in an attempt to develop a model system for this unique biological system. The mechanism of binding and reduction in the biological system has remained elusive, however, recently the crystal structure of the active site in nitrogenase was solved. It is believed that the substrate binding and reduction occur at the multimetallic site involved in the FeMo protein, which consists of Mo and Fe atoms bridged by sulfide ligands. (M. K. Chan et al., *Science*, 260, p. 792 (1993)). Additionally, nitrogenases have also been discovered which contain vanadium in place of molybdenum or only iron as the transition metal component. This suggests that a wide range of transition metals could potentially facilitate reactions of nitrogen in the coordination sphere. Towards this end, studies of the synthesis and reactions of $N_2$ complexes have been of particular interest in this field. In particular, this area emerged as a result of the discovery in 1965 by Allen and Senoff that $[Ru(NH_3)_5]^{2+}$ could reversibly coordinate dinitrogen. (A. D. Allen and C. V. Senoff, *J. Chem. Soc., Chem. Commun.*, p. 621, (1965)).

Since the initial discovery of a complex that could reversibly coordinate dinitrogen, a plethora of $N_2$ metal complexes have been isolated and characterized. $N_2$ is able to bond to a variety of metals with a variety of co-ligands. The nature of the bonding in these complexes varies, from end-on bonding in which the N≡N bond distance is similar to that in gaseous $N_2$ to linear end-on and side bridging to two or more metals. See, George et al. in "Modeling the N≡N Bond-Cleavage Step in the Reduction of Molecular Nitrogen to Ammonia", *Molybdenum Enzymes, Cofactors, and Model Systems*, Ch. 23, pp. 363–376 (1993).

Unfortunately, well-characterized synthetic systems capable of splitting $N_2$ have been elusive despite the multitude of known transition-metal complexes containing intact dinitrogen as a ligand. George et al. in "Reduction of Dinitrogen to Ammonia and Hydrazine in Iron(0) and Molybdenum(0) Complexes Containing the $N(CH_2CH_2PPh_2)_3$ Ligand" (*Inorg. Chem.* 34:1295–1298 (1995)) describes the reactions of $Fe(N_2)(NP_3)$ and $Mo(N_2)_2(NP_3)$ with HBr, where $NP_3$ is $N(CH_2CH_2PPh_2)_3$. Very low yields of hydrazine ($N_2H_4$) and $N_2$ were reported.

In all these complexes, there is no demonstrable activation of the N≡N triple bond. Further, the coordination number of the complexing metal is rather high and in all cases is greater than three, indicating that the metal is not in a very activated state. It is therefore desirable to develop a system having an activated nitrogen triple bond to permit product formation under mild conditions.

It is an object of the present invention to provide a process by which soluble, homogeneous metal complexes are capable of catalyzing the formation of ammonia at ambient temperatures and pressures. It is a further object of the present invention to provide a metal complex possessing an activated nitrogen triple bond which can readily undergo reaction with additional reagents. It is a further object of the invention to provide a metal complex capable of activating a nitrogen-nitrogen triple bond. It is a further object of the invention to provide a metal complex capable of activating a variety of small molecules for reaction with additional reagents.

SUMMARY OF THE INVENTION

In one aspect of the invention, a process is contemplated by which soluble, metal complexes are capable of effecting the formation of ammonia from dinitrogen. The metal complex comprises a three coordinate, low oxidation state transition metal complex. The metal complex comprises a metal selected from the group consisting of molybdenum, titanium, vanadium, niobium, tungsten, uranium and chromium, and a plurality of ligands coordinated to the metal such that the metal has a coordination number of no more than three, the ligand sufficiently bulky such that dimerization of the compound does not occur and characterized in that it does not undergo readily β-hydrogen elimination or cyclometallation reactions. A metal complex solution is exposed to dinitrogen under substantially atmospheric pressures and preferably at ambient temperatures, to obtain a metal-nitrido complex, whereby the oxidation state of the metal complex increases. The metal of the metal nitrido complex is then reduced in the presence of a hydrogen source, so as to obtain $NH_3$. Preferred embodiments include the use of hydrogen in the presence of a hydrogenation catalyst, or the use of an acid or reducing agent as the hydrogen source.

In another aspect of the invention, a metal compound is provided which is capable of reductive cleavage of the N≡N triple bond and reaction with other small molecules. The metal compound comprises a metal selected from the group consisting of molybdenum, titanium, vanadium, niobium, chromium, uranium and tungsten. The metal compound also includes a plurality of ligands coordinated to the metal such that the coordination number is no more than three. The ligand is sufficiently bulky that dimerization of the compound does not occur and is characterized in that it is not capable of a β-elimination reaction or cyclometallation reactions.

In another aspect of the invention, a metal compound for use in activation of small molecules comprises:

wherein M is a transition metal; and $R_1$ and $R_2$ are selected from the group consisting of tertiary alkyls, phenyls and substituted phenyls. In a preferred embodiment, $R_1$ is a tertiary alkyl group and $R_2$ is a phenyl or substituted phenyl group.

In preferred embodiments, the metal complex has the structure, $Mo(NRAr)_3$, where R is $C(CH_3)_3$ and Ar is $3,5-C_6H_3(CH_3)_2$, a synthetic three-coordinate molybdenum (III) complex. The formation of an intermediate complex was observed spectroscopically, and its conversion (with N≡N bond cleavage) to the nitrido molybdenum(VI) product N≡$Mo(NRAr)_3$ followed first-order kinetics at 30° C. The cleavage reaction proceeds by way of the complex $(\mu-N_2)\{Mo[N(R)Ar]_3\}_2$, which, according to EXAFS and NMR data, is formulated as a symmetrical bridging dinitrogen complex with a roughly linear MoNNMo core. (Laplaza et al., *J. Am. Chem. Soc.*, 118, 36, p. 8623 (1996))

"Coordination number", as that number is used herein, is number of atoms directly bonded to the metal of the complex.

BRIEF DESCRIPTION OF THE DRAWING

The invention is described with reference to the Drawing, in which.

DETAILED DESCRIPTION OF THE INVENTION

Figure 1:
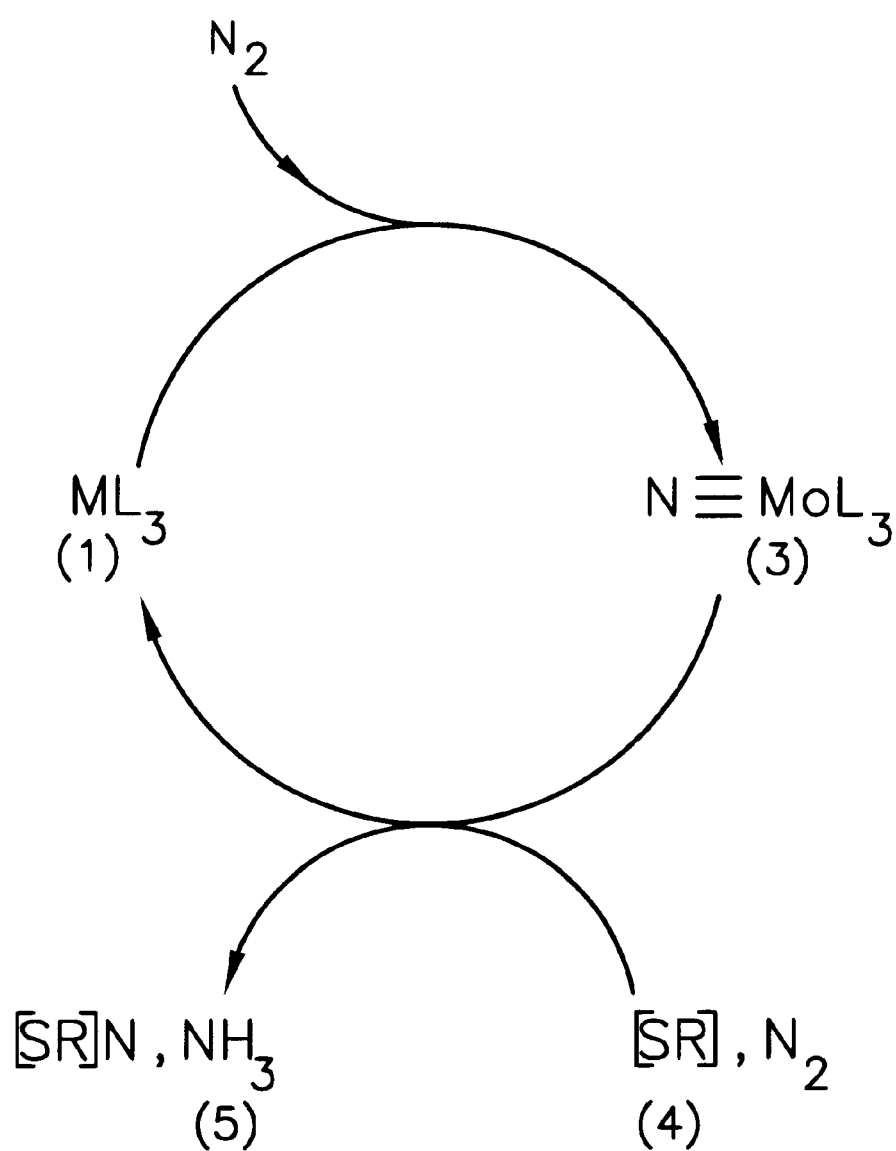
FIG. 1 is a reaction scheme for a catalytic reaction of $M(L)_3$ with dinitrogen for the generation of ammonia.

Many small molecules, and in particular dinitrogen, possess strong (and frequently unreactive) bonds. As an example of the stability of the nitrogen-nitrogen triple bond, a blanket of nitrogen is routinely used in the laboratory as an inert environment to prevent decomposition and/or reaction of labile and unstable compounds. In many instances, however, it would be desirable to activate such bonds to perform useful chemistry.

A particularly difficult task has been the generation of ammonia from dinitrogen under mild conditions. The immense concern with need for fertilized soil for food production led to the development of the current industrial method, the Haber-Bosch process. This process and its subsequent modifications are less desirable than a process that would effect the transformation of dinitrogen to ammonia under mild conditions. Although the mechanism of this transformation is not fully understood, it is believed that the nitrogen is first adsorbed onto the active heterogeneous metal catalyst, typically iron. The metal catalyst is activated by a high temperature process. The heterogeneous metal catalyst, in its activated state, then effects the cleavage of dinitrogen. Hydrogen is then adsorbed onto the catalyst and through subsequent steps reduces the adsorbed nitrogen to yield ammonia. This process, in effect, involves first the activation and cleavage of the dinitrogen bond, and subsequent reduction from a hydrogen source to yield the desired ammonia.

Unfortunately, although this process is the current method of choice, the use of heterogeneous catalysts are highly disadvantageous for several reasons. The reaction rate is limited to the surface area available, and often these surfaces are easily poisoned by external materials, thus blocking reactions with the desired substrates. Additionally, heterogeneous catalysts often do not give high selectivity in reactions, and many require intricate and costly reaction vessels. Significantly, heterogeneous catalysts often operate at very high temperatures and pressures, which pose economical, safety, and even environmental concerns. The cost of maintaining high temperatures and pressures can often be prohibitively high. Likewise, the maintenance of high temperatures and pressures requires a high energy consumption, and consequently a depletion of our valuable natural resources. Additionally, high temperatures and pressures pose grave safety concerns for the plant employees in charge of maintaining these conditions. Naturally, a reduction of the temperatures and pressures involved, as well as the elimination of costly and large reaction vessels used, would be desirable.

With this goal in mind, in one aspect of the present invention, a method is contemplated for the generation of ammonia from dinitrogen. This process represents a significant advancement over the Haber-Bosch process discussed above because the present invention has surprisingly found that a well-characterized homogeneous, low-coordinate, transition metal catalyst in solution at ambient temperatures and pressures may be used to split nitrogen. In preferred embodiments the transition metal is a three-coordinate complex and in a low oxidation state. The lower oxidation state of the metal leads to the greater reactivity of the metal because of the availability of electrons. Additionally, a lower coordination number ensures sufficient room for the dinitrogen molecule to bind and effect the subsequent cleavage of the dinitrogen molecule.

According to the method of the invention, ammonia may be generated from dinitrogen by reacting a three coordinate, low oxidation state transition metal complex with dinitrogen under substantially atmospheric pressures to obtain a metal-nitrido complex, whereby the oxidation state of the metal complex increases, and thereafter reducing the metal of the metal nitrido complex in the presence of a hydrogen source, so as to obtain $NH_3$. In a preferred embodiment, the metal complex includes a metal selected from the group consisting of molybdenum, titanium, vanadium, niobium, tungsten, uranium and chromium, and a plurality of ligands coordinated to the metal such that the metal has a coordination number of no more than three, the ligand sufficiently bulky such that dimerization of the compound does not occur and characterized in that it does not undergo readily β-hydrogen elimination or cyclometallation reactions.

The metal complex of the invention has been demonstrated to activate dinitrogen and other small molecules. This activation by the metal complex represents a first step in a process for the generation of ammonia from dinitrogen. The metal complex possesses a central metal which is a transition metal and which preferably is selected from the group consisting of molybdenum, titanium, vanadium, niobium, tungsten, uranium and chromium. The metal is in low oxidation state and hence, highly reactive. The valance state of the metal is selected such that the metal has a plurality and preferably at least three available electrons. In a bimetallic reaction, therefore, each metal complex contributes three of the six electrons required to cleave $N_2$. Thus a three-coordinate complex is desirably $d^3$ and the metal may have an oxidation state of $3^+$ or less. Additionally, the coordination number of the metal is low. This is related to the oxidation state of the metal (a highly coordinated metal tends to be at a higher oxidation state).

An open site is required at the metal to bind $N_2$. With coordination numbers greater than three it is expected the metal center would be too crowded. In preferred embodiments, the metal is molybdenum, titanium, vanadium, niobium, tungsten, uranium and chromium.

The ligands of the metal complex are selected to promote the reactivity of the metal center with dinitrogen. To that end, the ligand is sufficiently bulky such that no more than three ligand metal bonds are capable of formation. The ligand is further sufficiently bulky such that dimerization of the metal complex does not occur. The ligand is also selected such that it does not undergo readily β-hydride elimination or cyclometallation reactions.

Because the ligands are bulky, they prevent close approach to the metal center by other molecules. Thus, the metal center is incapable of undergoing those reactions typical of reactive metal centers, such as dimerization (through metal-metal centers or bridging ligands), phydrogen elimination and cyclometallation. Each of these reactions increase the coordination number and oxidation state of the metal center. Lastly, the ligand of choice should have the proper balance between electronegativity and electropositivity such that the ligand is neither a good leaving group (highly electronegative) or easily oxidized (highly electropositive).

In order to prevent β-hydrogen elimination, the ligand desirably possesses no β-hydrogen. β-Hydrogen elimination reactions involve the formation of a metal hydride bond and the elimination of a β-hydrogen from an alkyl ligand to form a metal π-bond, such as an alkene as shown in eq. (3)

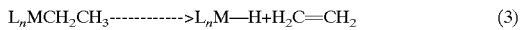

Competing reactions can also result from ligands that have no β-hydrogens, but that do have γ-, or δ-hydrogens, thus yielding cyclic products in a process known as cyclometalation. The reaction also is accompanied by an increase in coordination number and oxidation state of the metal, both of which have the effect of reducing its reactivity towards small molecules. In order to prevent cyclometallation reactions, CH moieties located four or more bond lengths from the metal center are to be avoided. Thus, any addition of the CH bond across the metal would result in a metallo ring of high ring strain, thereby discouraging such a reaction.

A metal complex meeting the criteria set forth above may be used in the ammonia generating method of the invention. The method of the invention includes a step of activating the dinitrogen molecule by reaction with the metal complex and subsequent cleavage of the dinitrogen molecule to yield a metal-nitrido complex. A second step of the method involves a reduction of the metal-nitrido complex in the presence of a hydrogen source, resulting in the cleavage of the metal-nitrido bond and generation of ammonia.

In the first step, the activation of the dinitrogen molecule to yield the metal nitrido complex is accomplished by exposing a solution of a metal complex which meets the structural and reactivity criteria set forth hereinabove to dinitrogen. The reaction may be accomplished using stoichiometric or catalytic amounts of the metal complex. The reaction proceeds under mild conditions of temperature and pressure. In one embodiment, the reaction proceeds at temperatures in the range of –30 to 65° C., and preferably in the range of 20 to 40° C., with an upper limit of 100°. In another embodiment, the reaction proceeds at ambient pressures, or at pressures slightly elevated. In a preferred embodiment, the reaction is carried out at about ambient pressures and temperatures. Slightly elevated temperatures may be used to increase reaction rates. An advantage of the present method is that the metal complex may be readily solubilized in standard organic solvents. This permits the reaction to be carried out in a homogeneous solution and overcomes many of the disadvantages of the heterogeneous Haber-Bosch process. The reaction may be carried in any liquid which is a solvent to the metal complex and can be carried out in almost any organic solvent, including solvents such as toluene, benzene, pentane, hexanes, ether and tetrahydrofuran.

In the second step, the metal-nitrido complex is reduced in the presence of a hydrogen source to yield ammonia. In one embodiment, generation of ammonia is accomplished by reaction of the metal-nitrido complex with an acid according to eq. (4),

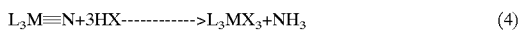

Suitable acids include those whose conjugate bases have a high affinity for the metal center. Acids such as hydrochloric acid, hydrobromic acid, hydrofluoric acid, nitric acid, sulfuric acid, trifluoromethanesulfonic acid, and phosphoric acid may be used. Reaction of the acid with the metal nitrido complex would take place in preferably in nonpolar solvents such as methylene chloride to yield ammonia at ambient temperatures and pressures.

In another preferred embodiments, ammonia may be generated by hydrogenation using a hydrogenation catalyst. Reactions involving the use of hydrogen could be carried out by bubbling hydrogen through a solution of the complex and methylene chloride, along with a suitable homogeneous hydrogenation catalyst such as Wilkinson's catalyst or a well-known heterogeneous catalyst. Much is known about the processes of homogeneous and heterogeneous hydrogenation and reference can be made to B. R. James in *Homogeneous Hydrogenation*, Wiley-Interscience, New York, 1973, or G. A. Somorajai, *Chemistry in Two Dimensions*, Cornell University Press, New York, 1981.

In another aspect of the present invention, it is contemplated to catalytically react dinitrogen with the reactive three coordinate complex of the invention. The catalytic cycle is shown in FIG. 1, in which $ML_3$ represents the reactive, low coordinate metal complex of the invention. $MoL_3$ 1 reacts with $N_2$ as described above to generate the metal nitrido complex $N\equiv MoL_3$ 3. The nitrogen is released from the newly reacted molybdenum-nitrido complex by reaction with a stoichiometric amount of a reducing agent 4 designated as [SR] in FIG. 1 in the presence of hydrogen and a hydrogenation catalyst. The reaction produces ammonia 5 in stoichiometric quantities. Thus, the overall synthetic route is:

$$3H_2 + N_2 \text{------>} 2NH_3 \quad (5)$$

Suitable stoichiometric reducing agents may be metals, such as aluminum and Wilkinson's catalyst used in the presence of $H_2$.

The criteria discussed previously for a metal complex capable of activating dinitrogen are also generally applicable to the activation of other small molecules. In yet another aspect of the invention, small molecules may be activated upon reaction with the three coordinate metal complex described in the invention. The following conditions set forth the preferred embodiments for such a reaction.

In one embodiment of the invention, an amino group possessing tertiary alkyl groups and/or aryl groups is selected. The selection of $R_1$ and $R_2$ is made to balance the electronegativity and electropositivity of the ligand. In preferred embodiments, $R_1$ is a tertiary alkyl group and $R_2$ is a phenyl or substituted phenyl group. Where $R_1$ and $R_2$ are both alkyl groups, the ligand may be too reducing. Likewise, where $R_1$ and $R_2$ are both aryl groups, the ligand may not have sufficient electron-donating capability. These imbalances may be compensated by appropriate substitution of the $R_1$ and $R_2$ group with electron donating and withdrawing groups. Suitable alkyl groups include "—$C(R_3)_3$", in which each $R_3$ is independently selected from the group of alkyls in the range of $C_1$ to $C_{10}$. Another preferred embodiment for the tertiary alkyl group is adamantyl, $C_{10}H_{15}$. Suitable aryl groups include phenyl and substituted phenyl groups. Phenyl substituents include, but are in no way limited to small alkyl groups in the range of $C_1$ to $C_{10}$, and halogens, such as F, Br, and Cl. Substitution may occur at any site. Substitution is selected to control both the bulkiness of the ligand and the electronegativity/electropositivity of the ligand.

A particularly preferred ligand for use in the invention is N-tert-butylanilide (—N(t-Bu)(Ph)). Other preferred ligands include 3,5-dimethyl-N-tert-butylanilide, 3,5-dimethyl-N-adamanyl anilide, and 4-fluoro-N-tert-butylanilide and combinations thereof.

A suitable metal is a transition metal which is capable of forming metal ligand complexes in a low valance state. The metal should also be capable of oxidation to a higher oxidation state commensurate with the degree of reduction of the reacting small molecule. Metals capable of a 3+ oxidation state to 6+ oxidation state are particularly desired. It is contemplated that Mo, Ti, V, W, Cr, Nb and U are suitable for use in the present invention. Molybdenum and tungsten are particularly preferred.

The metal compound as described herein is in a highly active state and yet, because of the bulkiness of the ligands, is unable to react readily with anything but very small molecules. Small molecules may approach the metal center, where larger molecules may not. As used herein, "small molecules" includes those molecules possessing a linear functionality consisting of two or more atoms. Suitable small molecules include, but are in no way limited to $N_2$, $N_2O$, alkyl and aryl azides NO, $NO_2$, $H_2$, $O_2$, $CO_2$, CO and the like.

As an example of the effectiveness of the complex of the present invention, monomeric $Mo(NRAr)_3$ (1) is formally related to the well-known dimeric Mo(III) complexes $X_3Mo\equiv MoX_3$ (X=alkyl, amide, alkoxide), which have unbridged metal-metal triple bonds. Severe stearic constraints (see FIG. 2) apparently render $Mo(NRAr)_3$ immune to dimerization, endowing the complex with the stored energy required for the observed reactivity toward $N_2$ and other small molecules.

Figure 3:
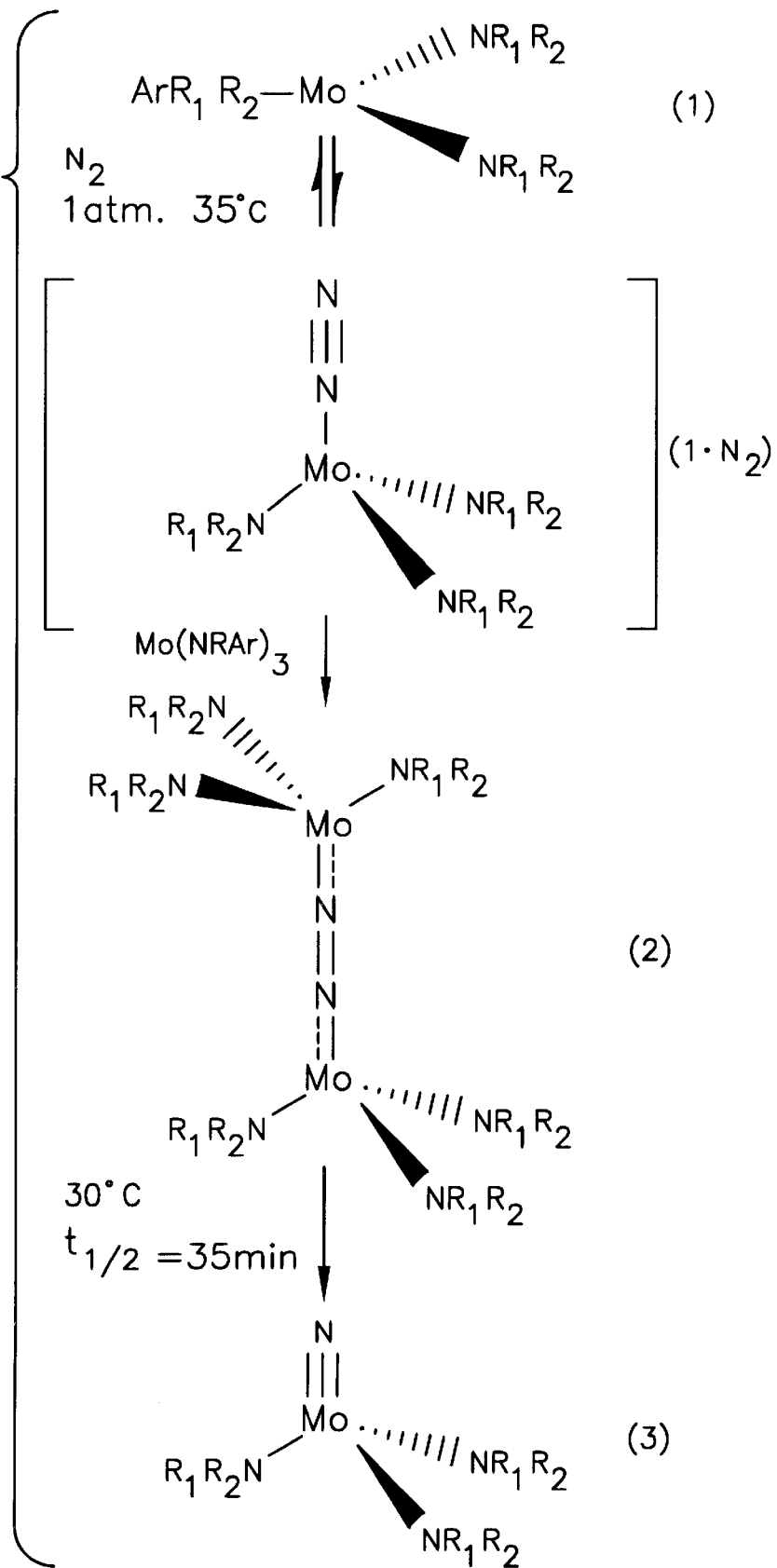
FIG. 3 is a reaction scheme for the reaction of $Mo(NR_1R_2)_3$ with dinitrogen.

Thus, small molecules are capable of interacting with the metal complex of the invention to form a reactive intermediate. A schematic diagram of the reaction is shown in FIG. 3 for the reaction of $Mo(NR_1R_2)_3$ 1, where $R_1$ is t-butyl and $R_2$ is phenyl, with dinitrogen. $Mo(NRAr)_3$ initially forms a dimolybdenum complex with a bridging dinitrogen ligand, 2, as shown in FIG. 3, which reacts further to form a molybdenum nitrido complex $N\equiv M(NRAr)_3$, denoted as 3 in FIG. 3.

While the cleavage of the $N\equiv N$ triple bond as shown in FIG. 3 results in the formation of a reactive metal-nitrido complex. Stable metal nitrido complexes are known, for example, $N\equiv Mo(X)_3$, where X=alkyl, amide or alkoxide. Thus, it is further within the scope of the invention to select a ligand which provides a metal nitrido complex which possesses a reactive metal-nitrido bond. The $M\equiv N$ triple bond is one of the strongest metal-ligand bonds, and its formation clearly provides the thermodynamic driving force for the $N_2$ cleavage reaction referred to here.

The metal-nitrido complex formed in the present invention, unlike those of the prior art, may be reacted with a wide variety of electrophiles. For example, $(R_1R_2N)_3Mo\equiv N$ can be reacted with methyl iodide to form a new carbon nitrogen bond in the complex $[(R_1R_2N)_3 Mo\equiv N-CH_3]I$. It is contemplated that other electrophiles may be used in the formation of complexes containing new carbon-nitrogen bonds. Suitable electrophiles include, but are in no way limited to RX (R=alkyl and X=halogen).

The invention may be further understood with reference to the following examples which are presented for the purposes of illustration only and which are in no way intended to be limiting of the invention.

EXAMPLE 1

Figure 2:
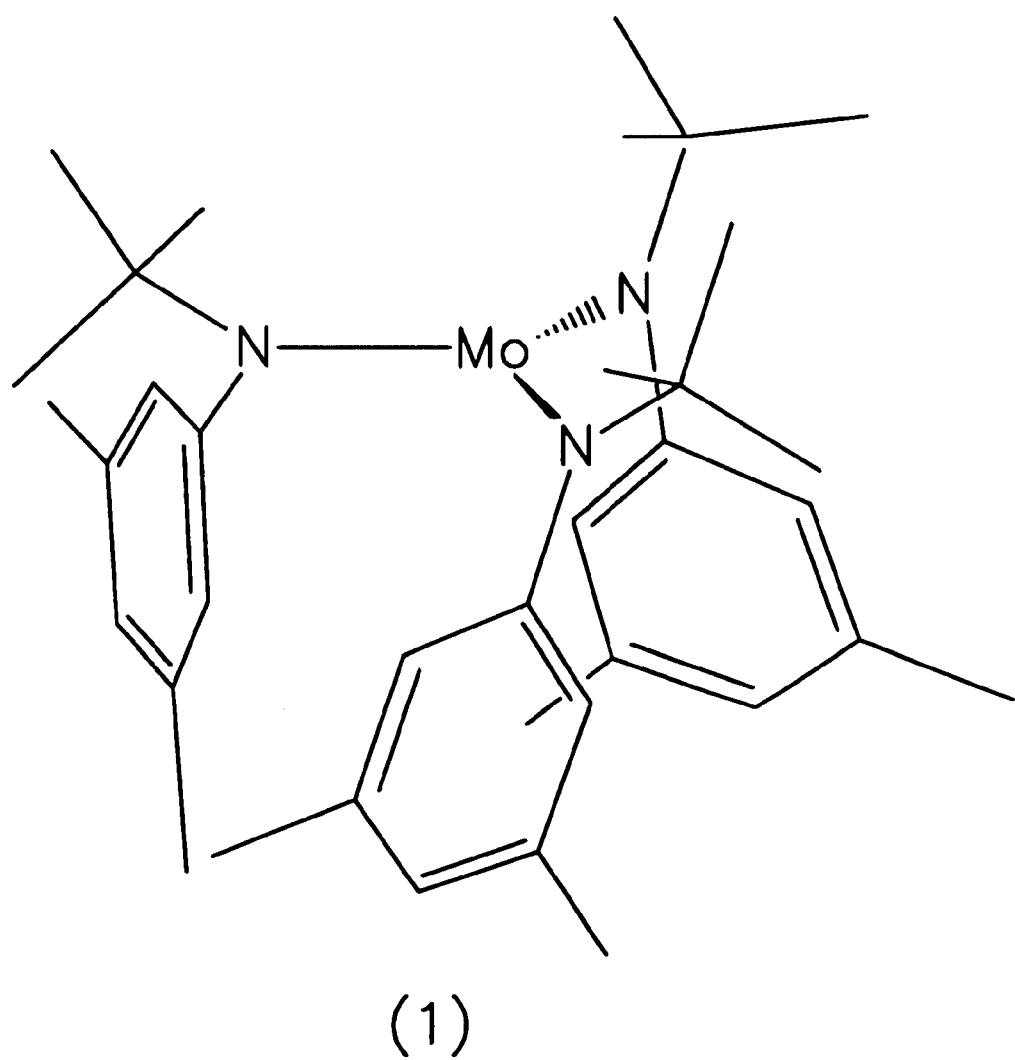
FIG. 2 is a line drawing of the molecular structure of a complex of the invention.

The synthesis and structural characterization of the three coordinate Mo(III) $Mo(NRAr)_3$ [where $R=C(CH_3)_2CH_3$ and $Ar=3,5-C_6H_3Me_2$ (Me, methyl), FIG. 2] is described.

In a typical preparation, $MoCl_3(THF)_3$ (4.164 mmol) and $Li(NRAr)(OEt_2)$ (8.315 mmol) were added to 70 mL of cold (−100° C.) ether, and the mixture was stirred for 2.5 h after warming to 28° C. The precipitated LiCl and excess $MoCl_3(THF)_3$ were removed by filtration. The filtrate was concentrated and cooled to −35° C. under an argon atmosphere to produce orange-red crystalline $Mo(NRAr)_3$ in 70% yield (mp 126–7° C.) (Laplaza et al., *J. Am. Chem. Soc.*, 117, p. 4999 (1995)).

EXAMPLE 2

The synthesis of the three coordinate Mo(III) complex, $Mo(NR_1R_2)_3$ is discussed in which $R_1=C(CH_3)_3CH_3$ and $R_2=4-C_6H_4F$.

MoCl$_3$(THF)$_3$ and Li(NR$_1$R$_2$)(OEt$_2$) are added to cold (−100° C.) ether, and the mixture is stirred for several hours after warming to room temperature. Precipitated LiCl and unreacted MoCl$_3$(THF)$_3$ are removed by filtration. The filtrate is concentrated and cooled to −35° C. in Argon to produce crystalline Mo(NR$_1$R$_2$)$_3$.

EXAMPLE 3

The synthesis of the three coordinate Mo(III) complex, Mo(NR$_2$R$_2$)$_3$ is discussed in which R$_1$=t-Bu and R$_2$=Ph.

Li[N(t-Bu)Ph](OEt)$_2$ and MoCl$_3$(THF)$_3$ are added sequentially to ether under argon. The stirred reaction mixture was sparged with argon for about one minute, and was then stirred for 2 hours. The mixture was filtered and was concentrated and cooled to yield burgundy crystalline Mo(NR$_1$R$_2$)$_3$.

EXAMPLE 4

The reductive scission of N$_2$ into two N$^{3-}$ ligands in its reaction with Mo(NRAr)$_3$ is described. The reaction occurs in hydrocarbon solution at low temperatures (−35° to 30° C.) and pressures (1 atm).

Mo(NRAr)$_3$ was prepared as described in Example 1. Placing Mo(NRAr)$_3$ under an atmosphere of N$_2$ (ethyl ether or benzene, 0.1 M, −35° C.) resulted in an intense purple solution in less than 45 min. Examination of the purple solutions by $^2$H nuclear magnetic resonance (NMR) spectroscopy revealed that the signal at 64 parts per million (ppm) for Mo(NRAr)$_3$ was being replaced by a single new peak at 14 ppm, attributable to a bridging dimer species 2, as shown in FIG. 3. When the reaction was carried out using pure Mo(NRAr)$_3$ in toluene (leaving all other conditions unchanged), from which the complex crystallizes less readily, complete conversion to 2 took approximately 48 hours at −35° C. On warming to 30° C., the purple solutions of 2 gradually became gold and lost their paramagnetism. Removal of all volatile material in vacuo left an amber crystalline residue that dissolved readily in benzene-d$_6$ for $^1$H NMR spectroscopic analysis. The $^1$H NMR spectroscopy showed that a terminal nitrido Mo(VI) complex (3, FIG. 3) had formed in essentially quantitative yield.

In a preparative-scale experiment, the nitrido complex 3 was isolated in 76% recrystallized yield from the reaction of Mo(NRAr)$_3$ (300 mg in 6 ml of toluene) with N$_2$ (1 atm). N$_2$ was verified as the source of the nitrido group by NMR studies using $^{15}$N$_2$.

The formation of purple 2 appears to proceed more rapidly at −35° C. than at room temperature (~28° C.); solutions of Mo(NRAr)$_3$ (ethyl ether, 01.M) do not turn purple when stored under N$_2$ (atm) at room temperature for 2 to 8 hours, and conversion to 3 is not appreciable ($\leq$5%) under these conditions. The more rapid N$_2$ uptake at −35° C. is likely to be a manifestation of the greater solubility of N$_2$ in organic solvents with decreasing temperature, which would lead to greater equilibrium concentrations of a mononuclear N$_2$ adduct (N$_2$)Mo(NRAr)$_3$ (1·N$_2$), the logical immediate precursor to 2.

EXAMPLE 5

The reductive scission of the N≡N triple bond in N$_2$O in its reaction with Mo(NRAr)$_3$ is described. The reaction occurs in hydrocarbon solution at low temperatures (−35° to 30° C.) and pressures (1 atm) (Laplaza et al., *J. Am. Chem. Soc.*, 117, p. 4999 (1995)).

Figure 4:
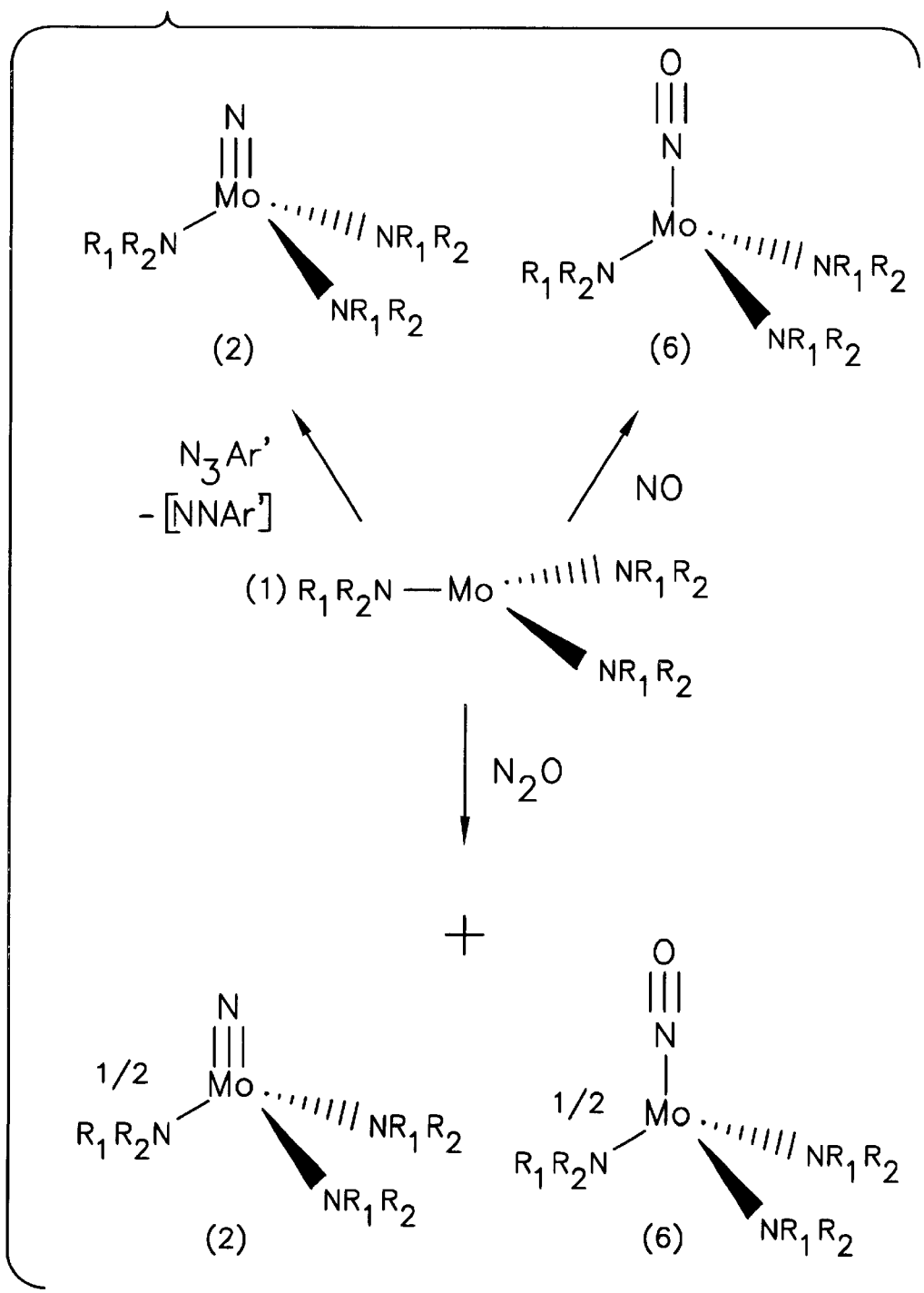
FIG. 4 is a reaction scheme for the reaction of $Mo(NR_1R_2)_3$ with nitrous oxide and aryl azides.

Mo(NRAr)$_3$ was prepared as described in Example 1. Exposure of a degassed solution of Mo(NRAr)$_3$ (0.157 mmol, 20 mL EtO$_2$, 25° C.) to an excess (3–4 equiv) of electronic grade N$_2$O resulted in a color change from red-orange to amber over 5–10 min. Upon removal of all volatile material in vacuo, a crystalline residue with a 1:1 ratio of the terminal nitrido complex, N≡Mo(NRAr)$_3$, and the nitrosyl complex (ON)Mo(NRAr)$_3$ was obtained. The reaction scheme is shown in FIG. 4.

EXAMPLE 6

The reductive scission of the N≡N multiple bond of an aryl azide in its reaction with Mo(NRAr)$_3$ is described. The reaction occurs in hydrocarbon solution at low temperatures (−35° to 30° C.) and pressures (1 atm).

Mo(NRAr)$_3$ was prepared as described in Example 1. Exposure of a degassed solution of Mo(NRAr)$_3$ (0.157 mmol, 20 mL EtO$_2$, 25° C.) to an excess of mesityl azide (0.997 mmol) resulted in a color change from red-orange to amber over 5–10 min. Upon removal of all volatile material in vacuo, a crystalline residue of the terminal nitrido complex, N≡Mo(NRAr)$_3$ was obtained. The reaction scheme is shown in FIG. 4.

EXAMPLE 7

A cyclic system for the scission of the N≡N triple bond is described. In this system it is shown that the molybdenum (III) starting material is regenerated, however, the system is only cyclic because less than 20% conversion was achieved. In a truly catalytic system more than one turnover of the catalyst system should be observed. In this system, turnover is defined as the production of one molecule of product for one molecule of reagent, or catalyst, used. For a discussion of the cyclic system see, Laplaza et al., "Nitrogen-Atom Transfer Coupled with Dinitrogen Cleavage and Mo—Mo Triple Bond Formation", *J. Am. Chem. Soc.*, Vol. 118, pp. 709–710 (1996), the entire contents of which are incorporated herein by reference. The interested reader is also directed to additional information described in Cummins et al., "Nitrogenation Versus Oxygenation of a 3-Coordinate Molybdenum(III) Complex", *Abstracts of Papers of the American Chemical Society*, Vol. 211, p.674-INOR (1996); and Johnson et al., "N and P Atom-Transfer", *Abstracts of Papers of the American Chemical Society*, Vol. 211, p.514-INOR (1996), the entire contents of both references are incorporated herein by reference.

We claim:

1. A metal-nitrido complex of the general formula:

wherein M is a Group 6 transition metal; R$_1$ is a tertiary alkyl or a substituted phenyl; and R$_2$ is a tertiary alkyl, a phenyl, or a substituted phenyl.

2. The metal-nitrido complex of claim 1, wherein R$_1$ is a tertiary alkyl and R$_2$ is a phenyl or a substituted phenyl.

3. The metal-nitrido complex of claim 1, wherein R$_1$ is a substituted phenyl and R$_2$ is a phenyl or a substituted phenyl.

4. The metal-nitrido complex of claim 1, wherein R$_1$ is a tertiary alkyl and R$_2$ is a tertiary alkyl.

5. The metal-nitrido complex of claim 2 or 4, wherein the tertiary alkyl is adamantyl or —C(R)$_3$, where R is a C$_1$ to C$_{10}$ carbon group.

6. The metal-nitrido complex of claim 5, wherein the tertiary alkyl is t-butyl.

7. The metal-nitrido complex of claim 2 or 3, wherein the substituted phenyl is substituted with an alkyl in the range of C$_1$ to C$_{10}$, or a halogen.

8. The metal-nitrido complex of claim 7, wherein the alkyl is a methyl.

9. The metal-nitrido complex of claim 7, wherein the halogen is fluorine, bromine, or chlorine.

10. The metal-nitrido complex of claim 1, wherein the metal is molybdenum, tungsten, uranium, or chromium.

* * * * *